(12) United States Patent
Vogel et al.

(10) Patent No.: US 9,861,292 B2
(45) Date of Patent: Jan. 9, 2018

(54) METHOD AND DEVICE FOR MEASURING BIO-IMPEDANCE DATA OF A PERSON

(71) Applicant: SECA AG, Reinach BL (CH)

(72) Inventors: Frederik Vogel, Hamburg (DE); Marc-Oliver Von Maydell, Hamburg (DE)

(73) Assignee: SECA AG, Reinach BL (CH)

( * ) Notice: Subject to any disclaimer, the term of this patent is extended or adjusted under 35 U.S.C. 154(b) by 134 days.

(21) Appl. No.: 14/114,581

(22) PCT Filed: Oct. 27, 2012

(86) PCT No.: PCT/DE2012/001061
§ 371 (c)(1),
(2) Date: Oct. 29, 2013

(87) PCT Pub. No.: WO2013/071908
PCT Pub. Date: May 23, 2013

(65) Prior Publication Data
US 2014/0073983 A1    Mar. 13, 2014

(30) Foreign Application Priority Data

Nov. 15, 2011   (DE) .......................... 10 2011 118 811

(51) Int. Cl.
| | |
|---|---|
| *A61B 5/05* | (2006.01) |
| *A61B 5/053* | (2006.01) |
| *A61B 5/00* | (2006.01) |
| *A61B 5/11* | (2006.01) |
| *A61B 5/0424* | (2006.01) |

(52) U.S. Cl.
CPC ............ *A61B 5/053* (2013.01); *A61B 5/0537* (2013.01); *A61B 5/0424* (2013.01); *A61B 5/1116* (2013.01); *A61B 5/4561* (2013.01); *A61B 5/4869* (2013.01); *A61B 5/4872* (2013.01); *A61B 5/6825* (2013.01); *A61B 5/6887* (2013.01)

(58) Field of Classification Search
CPC .................. A61B 5/053; A61B 5/0531; A61B 5/0536–5/0537; A61B 5/103; A61B 5/11; A61B 5/1116; A61B 5/1127–5/1128; A61B 5/4872; A61B 5/4869; A61B 5/6825; A61B 5/6887
USPC .......................... 600/547, 587, 592, 594, 595
See application file for complete search history.

(56) References Cited

U.S. PATENT DOCUMENTS

| | | | |
|---|---|---|---|
| 6,369,337 B1 | 4/2002 | Machiyama | |
| 7,262,703 B2 * | 8/2007 | Collins | ................ A61B 5/0537 340/539.12 |
| 8,577,439 B2 * | 11/2013 | Pinter | .................. A61B 5/0408 382/276 |
| 2004/0059242 A1 | 3/2004 | Masuo et al. | |

(Continued)

FOREIGN PATENT DOCUMENTS

CA        2269173        10/2000

*Primary Examiner* — Devin Henson
(74) *Attorney, Agent, or Firm* — Lucas & Mercanti, LLP; Klaus P. Stoffel

(57) ABSTRACT

A method and a device for determining biological impedance data of a person, in which least one impedance value is measured with the use of at least two electrodes and is transmitted to an evaluation unit. In the area of at least one output device, information concerning the person is made available for assuming an optimum body posture for the measurement of the biological impedance.

5 Claims, 4 Drawing Sheets

(56) References Cited

U.S. PATENT DOCUMENTS

| | | | | |
|---|---|---|---|---|
| 2005/0080353 A1* | 4/2005 | Whang | ............... | A61B 5/0537 600/547 |
| 2005/0182341 A1* | 8/2005 | Katayama | .............. | A61B 5/103 600/587 |
| 2010/0049037 A1* | 2/2010 | Pinter | ................. | A61B 5/0408 600/425 |
| 2010/0106045 A1* | 4/2010 | Sato | .................... | A61B 5/0537 600/547 |
| 2010/0312143 A1* | 12/2010 | Kim | .................... | A61B 5/0064 600/587 |
| 2010/0312148 A1 | 12/2010 | Sato | | |
| 2011/0237926 A1* | 9/2011 | Jensen | ................ | A61B 5/0537 600/393 |

* cited by examiner

_US 9,861,292 B2_

METHOD AND DEVICE FOR MEASURING BIO-IMPEDANCE DATA OF A PERSON

The present application is a 371 of International application PCT/DE2012/001061, filed Oct. 27, 2012, which claims priority of DE 10 2011 118 811.1, filed Nov. 15, 2011, the priority of these applications is hereby claimed and these applications are incorporated herein by reference.

BACKGROUND OF THE INVENTION

The invention relates to a method for determining the biological impedance of a person, wherein at least one impedance value is measured by using at least two electrodes and is transmitted to an evaluation unit.

Moreover, the invention relates to a device for determining the biological impedance values of a person, wherein the device has at least two electrodes for measuring at least one biological impedance value and the electrodes are coupled for transmitting measurement values to an evaluation unit.

Such methods and devices are typically carried out with the use of so-called body composition analyzers (BCA). Such devices are frequently equipped with two pairs of electrodes on which the person to be measured stands. Moreover, two additional electrodes are frequently provided for each hand of the person.

When using such devices and carrying out the method, it has been found that the quality of the measurement values is substantially influenced by the concrete body posture of the person. In the case of unfavorable body posture, measurement values can occur which lead to incorrect or imprecise measurement values.

SUMMARY OF THE INVENTION

Therefore, it is the object of the present invention to improve a method of the type mentioned in the introduction in such a way that the measuring accuracy is increased.

In accordance with the invention, this object is met by making available, in the area of at least one output device, information concerning the person for assuming an optimum body posture for measuring the biological impedance.

It is another object of the present invention to construct a device of the type mentioned in the introduction in such a way that the carrying out of precise measurements is reinforced.

In accordance with the invention this object is met in that the evaluation unit is coupled to an output unit, wherein the output unit is configured for making available information concerning an optimum body posture of the person.

The use of an output unit for making available information concerning a body posture of the person to be measured, makes it possible to provide the person with information concerning the assuming of a body posture or for correcting an already assumed body posture.

This can be carried out, for example, visually in the area of a display, acoustically, or by optically marking of the body parts to be positioned.

A good capacity for observation of the information is facilitated by visually representing the information.

In particular, an optimization of the body posture is reinforced by carrying out at least a partial measurement of an actual body posture of the person.

A simple realization by means of technical devices is reinforced by determining the body posture of the person by means of a camera.

In accordance with another embodiment, it is also being considered to determine the body posture through a mechanical measuring device, particularly a tactile device. In addition, by mounting movement sensors and/or triangulation, the position of the hand electrodes in space can be determined.

A further improvement of the measuring quality can be achieved by providing the information on the basis of a comparison of an actual body posture to a desired body posture.

BRIEF DESCRIPTION OF THE DRAWING

In the drawings, embodiments of the invention are schematically illustrated. In the drawing.

DETAILED DESCRIPTION OF THE INVENTION

Figure 1:
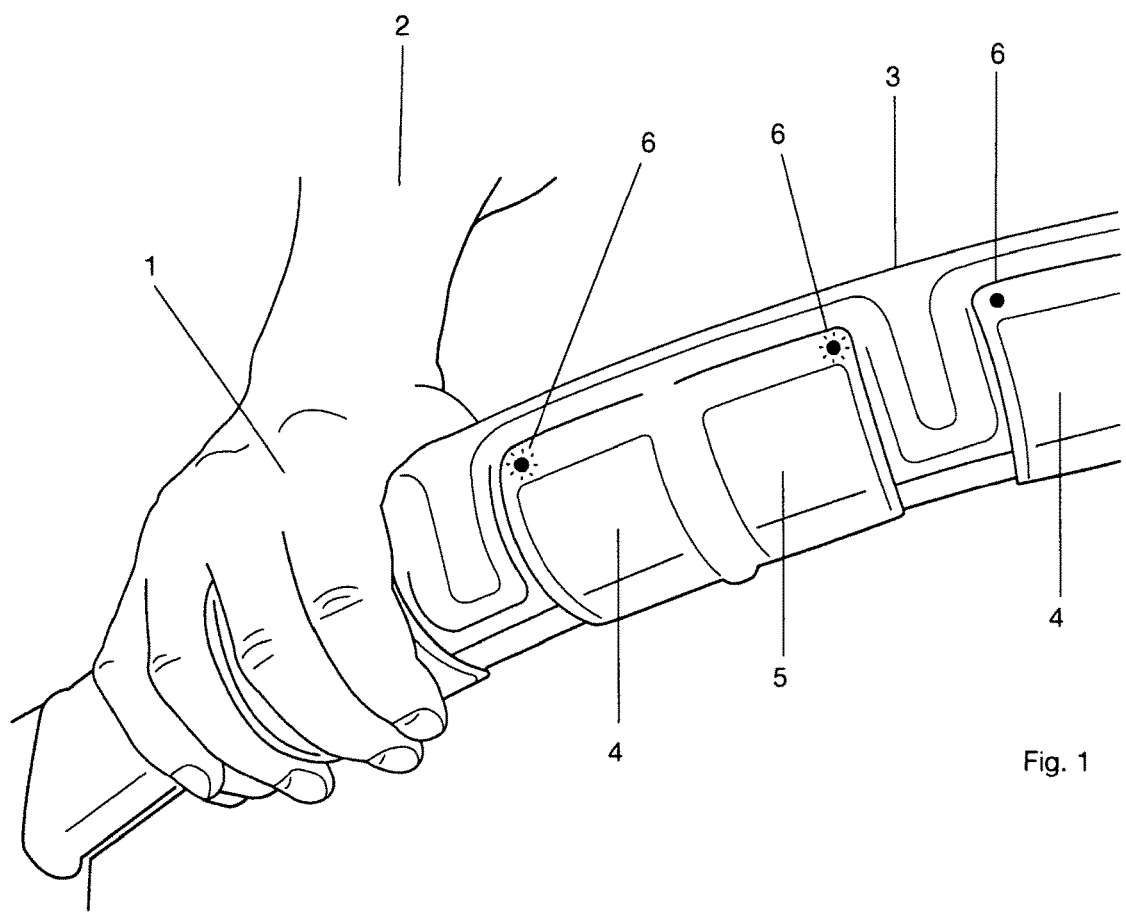
FIG. 1 shows a perspective partial illustration of a hand grip of a body composition analyzer.

In accordance with the illustration in FIG. 1, a hand 1 of a person 2 to be measured is positioned in the area of a grip 3 of a device for determining biological impedance data. In the area of the grip 3, a plurality of electrodes 4, 5 are arranged in pairs. At least in the area of several of the electrodes 4, 5, illuminating displays 6 are arranged, for example, light emitting diodes. Each electrode of the respective pairs of electrodes 4, 5 are dimensioned to be contactable by two fingers of the hand 1 of the person 2.

The illuminating displays 6 can, for example, by means of a green or red color, signal a correct or an incorrect positioning of the hand 1.

Figure 2:
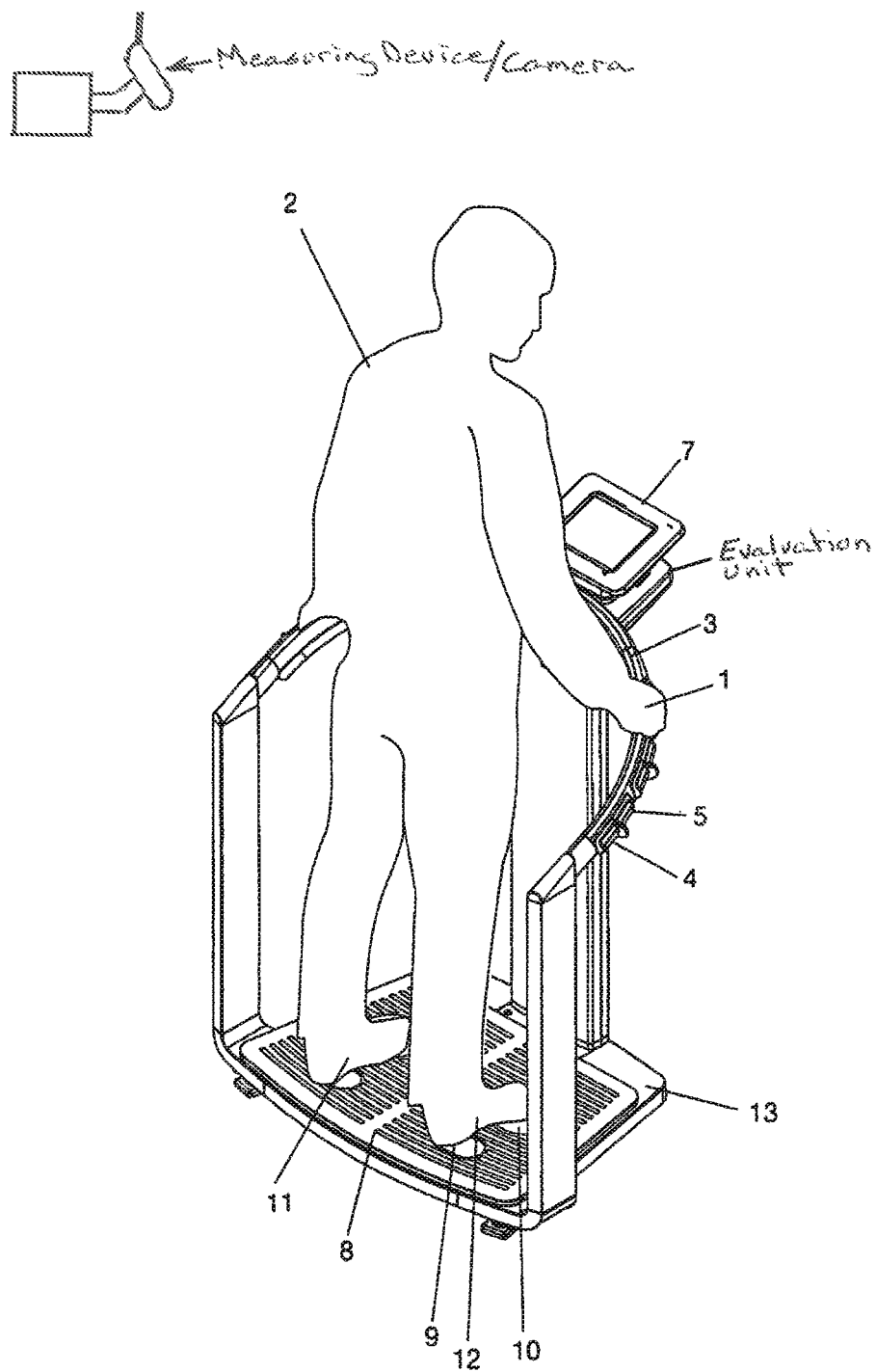
FIG. 2 is a perspective illustration of a person who stands on a body composition analyzer.

FIG. 2 is a schematic illustration of the person standing on the device for measuring biological impedance data. The person 2 has grasped the grip 3 in the area of several electrodes 4, 5. In viewing direction in front of the person 2, a display 7 can be seen. The display 7 may be for example, a screen or LED.

In the area of a standing surface 8, electrodes 9, 10 for the feet 11, 12 of the person 2 are arranged. A scale 13 for determining the weight of the person 2 may be positioned in the area of the standing surface 8.

In the illustrated embodiment, the grip 3 extends comparable to a railing in a semicircle. Moreover, the grip 3 is arranged inclined relative to the horizontal direction for reinforcing a positioning of the electrodes 4, 5 which is favorable for gripping.

Several pairs of electrodes 4, 5 may be arranged along the hand grip 3. In this connection each pair provides a position for the hands of the user. The correct body posture of the user can be obtained, for example, with the use of an electrical recognition of the respective pairs of electrodes contacting the person.

For example, it is possible in a first use by an assistant to determine a correct positioning for the hand of the person to be measured. This position can be stored, for example, in an electronic patient file. During the next use a comparison is made whether the respective user has once again contacted the electrodes in the position which is already known as being correct. A report back to the person to be measured or the assistant can be carried out, for example, in the area of hand grip 3 by illuminating green or red LED 6. When correctly positioned, the green LED would be controlled or when incorrectly positioned the red LED would be controlled.

Figure 3A:
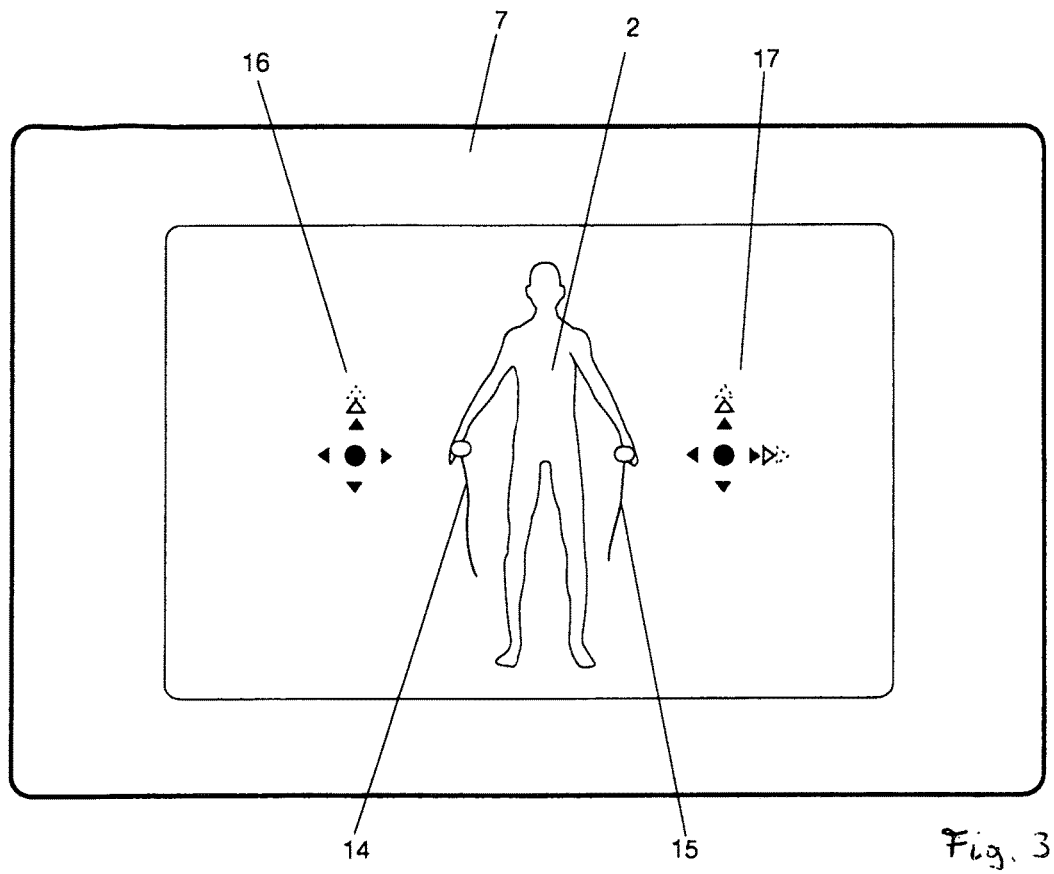
FIG. 3A is a schematic illustration of a visual display with indicators for a correction of the body posture.

FIG. 3A shows an indicator 7 constructed as a display with an illustration of a person 2 who has grasped the hand electrodes 14, 15. In the area of the indicator 7, correction displays 16, 17 are provided for the left and the right hand of the person 2. The correction displays 16, 17 may signal, for example, whether the respective hand should be raised or lowered to a greater extent, or whether the respective hand has to be positioned further to the left or to the right.

Figure 3B:
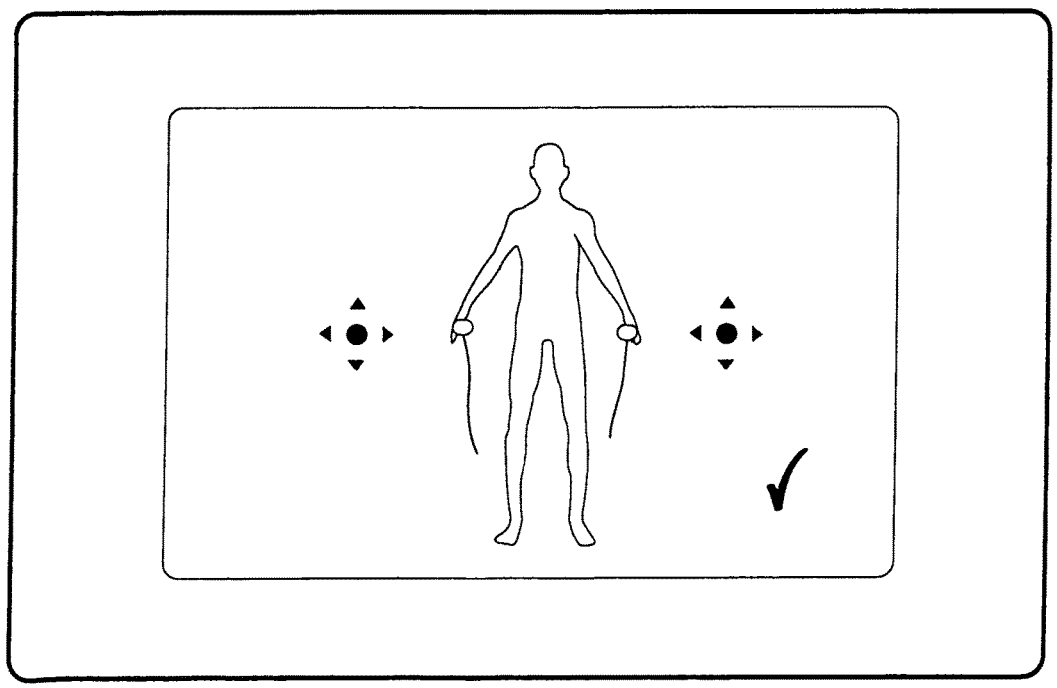
FIG. 3B illustrates a display in accordance with FIG. 3A with an indication concerning an already corrected body posture.

In accordance with the illustration in FIG. 3B, it is signaled that no correction of the hand position is required.

Figure 4:
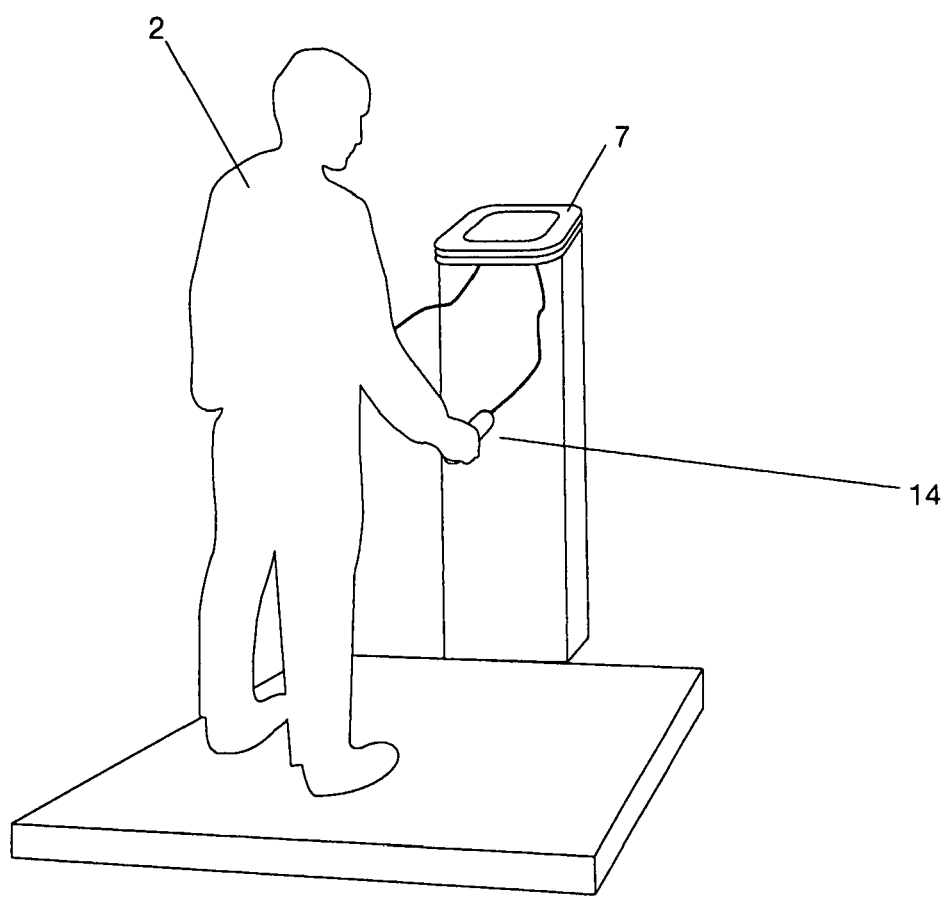
FIG. 4 is a perspective illustration of another device in which the person to be measured has grasped two hand grips.

FIG. 4 shows another person that holds a hand electrode 14 in the right hand.

Considered in particular is the use of contactless measuring devices. An optical measurement can be carried out with the use of a camera or without the use of a camera. For example, light barriers, laser scanners or carrying out a triangulation can be used. Also generally usable are electric measuring methods, as well as capacitive measurements. Another measurement can be carried out with the use of ultrasound.

The invention claimed is:

1. A device for determining biological impedance data of a standing person, the device comprising: two pairs of electrodes for each hand of the standing person for measuring at least one biological impedance value, wherein each of the two pairs of electrodes for each hand is arranged on a separate base element and the base elements are arranged on a support element so that the base elements are separated by a distance, the base elements being arranged symmetrically relative to a vertical mid-line of the support element, and each electrode is dimensioned to be contactable with two fingers of the person; at least two electrodes for each foot of the standing person for measuring at least one biological impedance value; an evaluation unit for transmitting measurement values, the electrodes being coupled to the evaluation unit; an output device for making available information concerning an optimum body posture of the person, the evaluation unit being coupled to the output device, wherein the output device is constructed for showing visual information on a display; at least one measuring device for determining an actual body posture of the person, wherein the evaluation unit is operatively constructed to carry out a comparison between a desired value and an actual value with respect to body posture of the person; and, an electronic storage device that stores data identifying the person, data regarding a desired body posture of the person and data regarding electrodes contacted by the person when the person is correctly positioned so that with a renewed use of the device for determining biological impedance data by the person an actual occupied body posture and actual contacted electrodes are identified and the output device directs the person with corresponding indicators to assume positions dictated by the stored data, within a maximum allowable deviation, wherein the display is configured to show corrective information at least for adjustments of a horizontal position of the hands of the person relative to the pairs of electrodes to be used by the person, wherein the device for determining biological impedance data is a body composition analyzer.

2. The device according to claim 1, wherein the measuring device is a camera.

3. The device according to claim 1, wherein the measuring device is a mechanical measuring device.

4. The device according to claim 1, wherein the measuring device is a contactless measuring device.

5. The device according to claim 1, comprising three pairs of electrodes for each hand of the standing person, each pair of electrodes being arranged on a separate base element.

* * * * *